United States Patent [19]

Mutsers et al.

[11] Patent Number: 4,675,440
[45] Date of Patent: Jun. 23, 1987

[54] PROCESS FOR PREPARING PURIFIED, VIRTUALLY ODORLESS SOLID BENZOIC ACID

[75] Inventors: Stanislaus M. P. Mutsers; Michael H. Willems, both of Geleen; Wilhelmus P. Wolvers, Landgraaf, all of Netherlands

[73] Assignee: Stamicarbon B.V., Geleen, Netherlands

[21] Appl. No.: 816,055

[22] Filed: Jan. 3, 1986

[30] Foreign Application Priority Data

Jan. 11, 1985 [NL] Netherlands .......................... 8500060

[51] Int. Cl.[4] .............................................. C07C 51/42
[52] U.S. Cl. ..................... 562/494; 562/412; 562/415
[58] Field of Search .......................................... 562/494

[56] References Cited

U.S. PATENT DOCUMENTS 4,227,018 10/1980 Wolf ..................................... 562/494
4,547,587 10/1985 Kleintjens ........................... 562/494

Primary Examiner—Paul J. Killos
Attorney, Agent, or Firm—Cushman, Darby & Cushman

[57] ABSTRACT

The invention relates to a process for preparing purified, virtually odorless, solid benzoic acid obtained from toluene by oxidation with a gas containing molecular oxygen, by means of a treatment using an inert gas or gas mixture, wherein the benzoic acid to be purified is supplied in a liquid state to a fluid or spouted bed granulator in which the prevailing temperature is below the solidification temperature of the benzoic acid and in which the benzoic acid is treated, during and possibly after the granulating process, with the said gas or gas mixture, the impurities present being taken up in whole or in part in the gas or gas mixture, upon which the benzoic acid thus purified is removed from the fluid or spouted bed device.

5 Claims, No Drawings

PROCESS FOR PREPARING PURIFIED, VIRTUALLY ODORLESS SOLID BENZOIC ACID

The invention relates to a process for preparing purified, virtually odourless, solid benzoic acid obtained from toluene by oxidation with a gas containing molecular oxygen, by means of a treatment using an inert gas or gas mixture.

Such a process is known from the German patent specification 2460822, in which a process is described for the after-treatment of prilled benzoic acid with a heated inert gas, usually under atmospheric conditions, for the purpose of recovering the benzoic acid from a mixture of benzoic acid and biphenyls. The disadvantage of that process is that generally the duration of the said after-treatment is long, while for the after-treatment a separate column is required in which the treatment is usually carried out batchwise.

The object of the invention is to provide a process for purifying benzoic acid that can be carried out continuously, in which process a separate after-treatment has become superfluous, the purification of the benzoic acid and its granulation being effected in one apparatus, and in which process the costs of the apparatus have been substantially reduced compared with the prilling device.

The invention therefore relates to a process for preparing purified, virtually odourless, solid benzoic acid obtained from toluene by oxidation with a gas containing molecular oxygen, by means of a treatment using an inert gas or gas mixture, the process being characterized in that the benzoic acid to be purified is supplied in a liquid state to a fluid or spouted bed granulator in which the prevailing temperature is below the solidification temperature of the benzoic acid and in which the benzoic acid is treated, during and possibly after the crystallization process, with the said gas or gas mixture, the impurities present being taken up in whole or in part in the gas or gas mixture, after which the benzoic acid thus purified is removed from the fluid or spouted bed device.

By applying the process according to the invention granulation and extraction are combined, the impurities being removed already during the granulation and that to such a degree that a virtually odourless benzoic acid is obtained.

The granulation of a substance in a fluid or a spouted bed device is known per se from, for instance, Kirk-Othmer, Encycl. of Chem. Technology 3(21) pages 98-99. It has now been found, however, that during the process of granulating, in a fluid or spouted bed installation, biphenyl-contaminated benzoic acid obtained by oxidation of toluene there will not only be a shaping of benzoic acid solids, but surprisingly also a purification of the benzoic acid supplied, the impurities present being taken up in and entrained with the gas or gas mixture in whole or in part, thus leaving the device in a gaseous form.

The inert gas applied may be any gas that does not react with benzoic acid, for instance nitrogen, carbon dioxide, noble gases or a mixture of various gases. Owing to the risk of explosion, air is usually not suitable as an inert gas. However, and air/nitrogen mixture with an oxygen content lower than the 10% (vol.) limit, below which explosions are no longer to be feared, is particularly effective.

The amount of gas or gas mixture used in a process according to the invention may be chosen, for instance, between 1 and 500 $Nm^3$ (NPT) gas per kg benzoic acid and is determined on the one side by the degree of purification aimed at and on the other by the fact that the criteria for a fluid or spouted bed must be complied with.

The temperature to be applied in a process according to the invention must not be higher than the solidification temperature of the benzoic acid. The lower temperature limit is determined by the fact that at a low temperature the rate of diffusion of the impurities in the benzoic acid, and particularly that of the biphenyls, will be too low, and hence the duration of the treatment too long, and the required size of the apparatus will increase strongly. Preference is therefore given to applying, in a fluid or spouted bed granulator, a temperature of 50°-100° C.

The pressure to be applied in the process according to the invention is not essential. Pressures of 0.1-10 MPa are suitable and working at a pressure at least equalling 0.9 time the critical pressure of the gas or gas mixture to be applied is not even ruled out in so far as the reduced temperature of the gas or gas mixture (which is by definition the ratio between the process temperature and the critical temperature, both in Kelvin) has a value preferably higher than 0.9, so that the extraction/granulation process takes place under near-critical circumstances.

The invention is elucidated by means of the following non-restrictive examples. The examples are based on benzoic acid having an impurities content of 0.03% (wt) diphenyl oxide, 0,04% (wt) 2-methyldiphenyl (2-MDP) and 0.16% (wt) 3-methyl and 4-mehyldiphenyl (3- and 4-MDP) combined.

EXAMPLE 1

To a continuous fluid bed granulator having a circular diameter of 45 cm, provided with a perforated bottom plate in which holes with a diameter of 1.8 mm have been made in a regular triangular pattern so that 6% of the bottom plate consists of these holes, 100 kg/h benzoic acid with a temperature of 130° C. is supplied through a central feeder. To the fluid bed, having a temperature of 80° C., an air/nitrogen mixture with 7.5% (vol) oxygen, having a temperature of 45° C., is supplied as fluidizing gas so that the superficial velocity of this gas in the bed is 2 m/s. At 70 cm above the bottom plate there is a radial overflow for carrying off the granulated product. At the top surface of the fluid bed the prevailing pressure is 0.1 MPa, while the pressure drop over the bottom plate is 2 kPa and over the fluid bed 3 kPa. The central feeder is in the form of a two-phase sprayer consisting of a central liquid feeder with a diameter of 4 mm surrounded by a cylindrical casing through which an air-nitrogen mixture with 7.5% (vol) oxygen is supplied in an amount of 100 kg/h with a temperature of 130° C. and a superficial velocity in the casing of 300 m/s.

The particles leaving the fluid bed via the overflow are classified by means of a horizontal deck screen. Particles with dimensions smaller than 2 mm are recirculated to the fluid bed. Particles with dimensions between 2 and 4 mm constitute the final product and particles with dimensions larger than 4 mm are reduced in size by means of a double rolling crusher with scraper to form particles having an average size of about 1 mm, which are successively recirculated to the fluid bed.

The resulting final product of purified benzoic acid is found on analysis yet to contain 0.02% (wt) 3 and 4 MDP, while the presence of the other impurities can no longer be demonstrated.

EXAMPLE 2

To a continuously operated spouted bed granulator, consisting of a cylindrical vessel with a diameter of 45 cm and a height of 175 cm, provided at the bottom with a conical section forming an angle of 30° with the vertical and provided with a central spout-gas feeder with a diameter of 6.5 cm, 600 kg/h of an air/nitrogen mixture with 8.5% (vol) oxygen with a temperature of 30° C. and 100 kg/h benzoic acid with a temperature of 130° C. are supplied. The superficial velocity of the gas in the spout is about 40 m/s. The benzoic acid is sprayed in a liquid state in the throat of the spout. The spouted bed is operated under a pressure of 0.1 MPa and at a temperature of 70° C. At a height of 30 cm from the bottom of the cylindrical part of the granulator there is a radial overflow for carrying off the granulated product. The product thus obtained is classified and recovered, respectively recirculated, in the same way as in example 1.

The resulting final product of purified benzoic acid is found on analysis yet to contain 0.03% (wt) 3 and 4 MDP, while the presence of the other impurities can no longer be demonstrated.

We claim:

1. Process for preparing purified, virtually odourless, solid benzoic acid obtained from toluene by oxidation with a gas containing molecular oxygen, by means of a treatment using an inert gas or gas mixture, the process being characterized in that the benzoic acid to be purified is supplied in a liquid state to a fluid or spouted bed granulator in which the prevailing temperature is below the solidification temperature of the benzoic acid and in which the benzoic acid is treated, during and possibly after the granulating process, with the said gas or gas mixture, the impurities present being taken up in whole or in part in the gas or gas mixture, upon which the benzoic acid thus purified is removed from the fluid or spouted bed device.

2. Process according to claim 1, characterized in that the gas or gas mixture consists of an air-nitrogen mixture the oxygen content of which is lower than 10% (vol).

3. Process according to claims 1-2, characterized in that the applied flow rate of the gas is 1 to 500 Nm$^3$ (NPT) gas per kg benzoic acid.

4. Process according to claims 1-3, characterized in that the temperature applied in the fluid or spouted bed granulator is 50°-100° C.

5. Process according to claims 1-4, characterized in that the pressure in the device is at leat 0.9 time the critical pressure and the temperature in the device is at least 0.9 time the critical temperature (both temperatures in Kelvin) of the gas or gas mixture.

* * * * *